US00PP13296P2

(12) United States Plant Patent
Zary

(10) Patent No.: US PP13,296 P2
(45) Date of Patent: Dec. 3, 2002

(54) HYBRID TEA ROSE PLANT NAMED 'JACSALL'

(75) Inventor: Keith W. Zary, Thousand Oaks, CA (US)

(73) Assignee: Jackson & Perkins Wholesale, Inc., Medford, OR (US)

( * ) Notice: Subject to any disclaimer, the term of this patent is extended or adjusted under 35 U.S.C. 154(b) by 12 days.

(21) Appl. No.: 09/696,344

(22) Filed: Oct. 24, 2000

(51) Int. Cl.[7] ..... A01H 5/00
(52) U.S. Cl. ..... Plt./132
(58) Field of Search ..... Plt./132

*Primary Examiner*—Bruce R. Campell
*Assistant Examiner*—Susan B. McCormick
(74) *Attorney, Agent, or Firm*—Klarquist Sparkman, LLP

(57) ABSTRACT

Hybrid tea rose plant having the high centered buds fully open to vary large flowers and dark green, leathery foliage resistant to rust and powdery mildew.

1 Drawing Sheet

The present invention relates to a new and distinct variety of rose plant of the hybrid tea class which was originated by me by crossing the variety 'KRIcarlo', U.S. Plant Pat. No. 5,165, with an unnamed seedling.

The primary objective of this breeding was to produce a new rose variety having the high centered flower form of the female parent and the very long flower life and excellent disease resistance of the male parent. The objective was substantially achieved, along with other desirable improvements, as evidenced by the following unique combination of characteristics that are outstanding in the new variety and that distinguish it from its parents, as well as from all other varieties of which I am aware:

1. Very high, fully open flowers;
2. High centered buds and half open form;
3. Dark green, leathery foliage; and
4. Resistance to powdery mildew and rust.
5. 'JACsall' differs from its female parent 'KRIcarlo' in that the parent has smaller flowers with smaller petals and has smaller foliage than 'JACsall'.
6. The male parent has pink flowers with fewer petals that the flowers of 'JACsall' and the parent also has more prickles.

Asexual reproduction of this new variety by budding, as performed at Wasco, Calif., shows that the foregoing and all other characteristics and distinctions come true to form and are established and transmitted through succeeding propagations.

The accompanying illustration shows typical specimens of the vegetative growth and flowers of this new variety in different stages of development, depicted in color as nearly true as it is reasonably possible to make the same in color illustration of this character.

The following is a detailed description of my new rose cultivar with color descriptions using terminology in accordance with The Royal Horticultural Society (London) Colour Chart (1966), except where ordinary dictionary significance of color is indicated.

Parentage:
*Seed parent.*—'KRIcarlo' (U.S. Plant Pat. No. 5,165).
*Pollen parent.*—Unnamed seedling.

Classification:
*Botanical.*—*Rosa hybrida.*
*Commercial.*—Hybrid tea.

FLOWER

Observations made from specimens grown in a garden environment at Somis, Calif., January, 1999 to July, 2000.

Blooming habit: Continuous.
Bud:
*Size.*—One and three-quarter inches long when the petals start to unfurl.
*Form.*—The bud form is long, pointed ovoid.
*Color.*—When sepals first divide, bud color is Red Group 50A. When half blown, the upper sides of the petals are Red Group 50B except near the base where they are Red Group 50C; and the lower sides of the petals are Red Group 50C except near the base where they are Red Group 50D.
*Sepals.*—Color: Green Group 138B except where exposed to bright sunlight, then Greyed-Purple Group 185A. Surfact texture: Covered in fine hairs. Length: 1½ inches–1¾ inches. Width: ⅝ inch–¾ inch. There are three normally appendaged sepals. There are two unappendaged sepals with ciliolate edges.
*Receptacle.*—Color: Green Group 137C except when exposed to bright sunlight, then Greyed-Purple 183A. Shape: Funnel. Size: Large, about ⅝"×⅜". Surface: Smooth.
*Peduncle.*—Length: Medium, averaging about 3 to 3½ inches. Surface: Smooth with a few small glands. Color: Green Group 137D except when exposed to bright sunlight, then Greyed-Purple Group 183A. Strength: Stiff, erect and heavy.
Bloom:
*Size.*—Very large. Average open size is 5½ to 6 inches.
*Borne.*—Singly.
*Stems.*—Strength: Strong. Average length is about 16 to 20 inches; Diameter: 1⁵⁄₁₆ inches–1⅜ inches.
*Form.*—When first open: Bloom is high centered. Permanence: Flattens and outer petals curl back.
*Petalage.*—Number of petals under normal conditions: 40–45.

*Color.*—The upper sides of the petals are Red Group 50B except for the lower third of the petals which are Red Group 50C. The reverse sides of the petals are Red Group 50C except for the lower third of the petals which are Red Group 50D. The base of each petal has ¼"×¼ Yellow Group 6C color spot. The major color on the upper side is Red Group 50B.

*Variegations.*—Occasional whitish streak on the outer petals (near Yellow-White Group 158C).

*Discoloration.*—The general tonality at the end of the first day: No change. At the end of the third day: A fading in bright light on the exposed petal edges of Red Group 50D.

*Fragrance.*—Moderate, spicy.

Petals:

*Texture.*—Thick, leathery, (i.e., coriaceous).

*Shape.*—Round to deltoid.

*Size.*—Length 1 7/16 inches–2 inches. Width: 1⅝ inches–1 15/16 inches.

*Form.*—Tips slightly recurved, edges slightly quilled.

*Arrangement.*—Imbricated. Petaloids in the center are few (0–7) Red Group 50B in color and range from ⅛"×¼ to ½×1" in size.

*Persistence.*—Petals drop off cleanly before drying.

*Lastingness.*—On the plant: Fair (about 5–6 days). As a cut flower: Fair (about 6 days).

Reproductive parts:

*Stamens.*—Number: 120–150.

*Anthers.*—Length: 1/16 inch–3/32 inch. Color: Yellow-Orange Group 19C. Arrangement: Regular round styles.

*Filaments.*—Color: Red Group 36C. Length: ⅛ inch–3/16 inch.

*Pollen.*—Color: Greyed-Orange Group 164C.

*Pistils.*—Number: 60–80.

*Styles.*—Color: Red Group 45C. Length: 3/32 inch.

*Stigmas.*—Color: Yellow-White Group 159B. Length: 1/32 inch.

*Hips.*—None observed.

Plant:

*Form.*—Bush.

*Growth.*—Vigorous, upright, branching. At maturity, height is 5½ feet, width is 4 feet.

Foliage: Number of leaflets on normal mid-stem leaves: 5 to 7.

*Size.*—Large (7½ inches long×5½ inches wide).

*Quantity.*—Normal; typical of a hybrid tea.

*Color.*—New foliage: Upper surface: Greyed-Purple Group 183A. Lower surface: Greyed-Purple Group 183D. Old foliage: Upper surface: Green Group 139A. Lower surface: Green Group 138B.

Leaflets:

*Shape.*—Pointed oval.

*Texture.*—Lusterous.

*Edge.*—Serrated.

*Serration.*—Single, small.

*Petiole.*—Length: 2¾ inches. Prickles: None.

*Petiole rachis.*—Color: Upper surface: Greyed-Red Group 178A; Lower surface: Green Group 138B. Length: 4½ inches.

*Petiole rachis underside.*—Rough, typically with three downwardly hooked 1/16 inch prickles.

*Stipules.*—Long, serrated (about 1 inch); bearded; glandular.

*Disease resistance.*—Resistant to mildew and rust, susceptible to blackspot under normal growing conditions.

Wood:

*New wood.*—Color: Greyed-Purple Group 183A. Bark: Smooth.

*Old wood.*—Color: Green Group 137C. Bark: Smooth.

Prickles:

*Quantity.*—On main canes from base: Many. On lateral from main canes: Many.

*Form.*—Medium, straight to hooked slightly downward. Length: ¼ inch–½ inch.

*Color when young.*—Greyed-Purple Group 183A.

*Color when mature.*—Greyed-Orange Group 165C.

Small Prickles:

*Quantity.*—On main stalks: None. On laterals: None.

Hardiness: Winter hardy to Zone 5. It has no drought tolerance but thrives in daytime temperatures up to 115° F. and night time temperatures no higher than 90° F.

I claim:

1. A new and distinct variety of rose plant of the hybrid tea class, substantially as herein shown and described, characterized particularly by having its high centered buds which fully open to very large flowers and its dark green, leathery foliage having resistance to rust and powdery mildew.

* * * * *

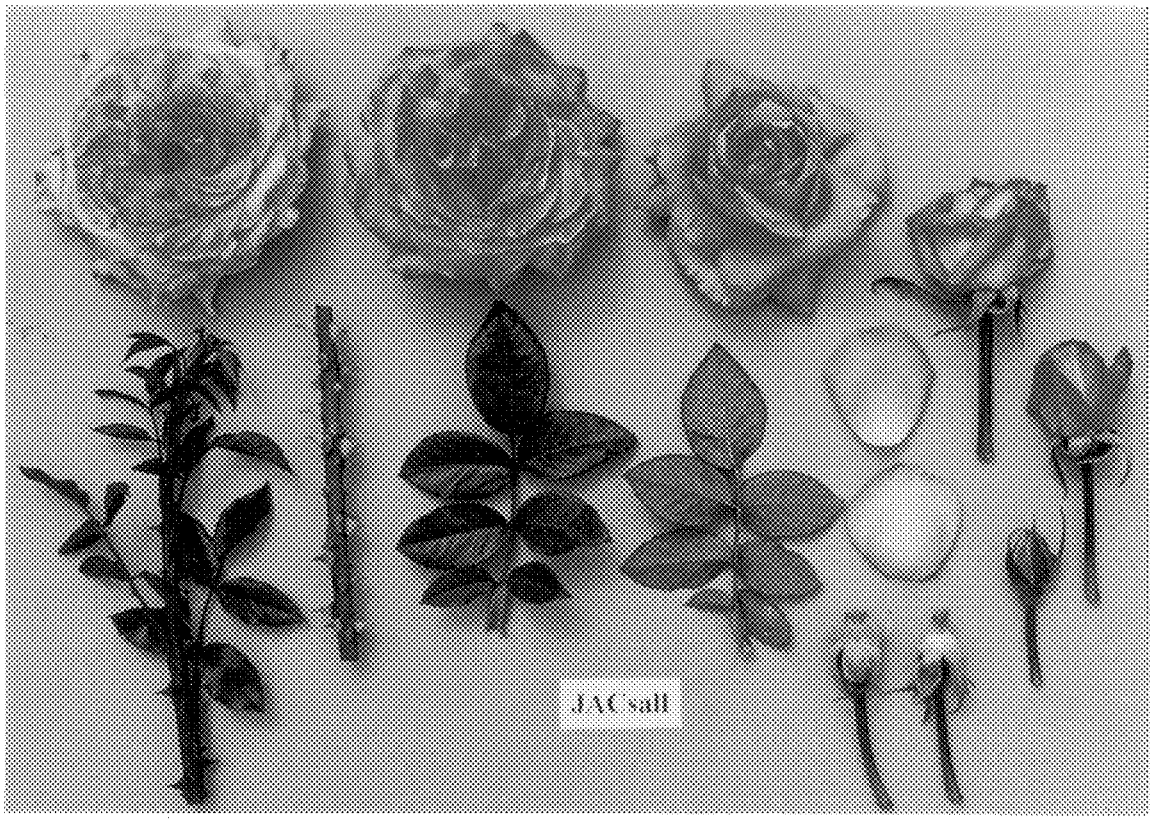
JAGsall